US011458239B2

(12) United States Patent
Grober

(10) Patent No.: US 11,458,239 B2
(45) Date of Patent: Oct. 4, 2022

(54) DEVICE FOR CLAMPING A HOSE LINE, MEDICAL TREATMENT DEVICE WITH A DEVICE FOR CLAMPING A HOSE LINE, AND METHOD FOR MONITORING A DEVICE FOR CLAMPING A HOSE LINE

(71) Applicant: FRESENIUS MEDICAL CARE DEUTSCHLAND GMBH, Bad Homburg (DE)

(72) Inventor: Tobias Grober, Heusenstamm (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 377 days.

(21) Appl. No.: 16/487,102

(22) PCT Filed: Feb. 20, 2018

(86) PCT No.: PCT/EP2018/054182
§ 371 (c)(1),
(2) Date: Aug. 20, 2019

(87) PCT Pub. No.: WO2018/153875
PCT Pub. Date: Aug. 30, 2018

(65) Prior Publication Data
US 2020/0338332 A1 Oct. 29, 2020

(30) Foreign Application Priority Data

Feb. 23, 2017 (DE) ..................... 10 2017 001 744.1

(51) Int. Cl.
*F16K 7/04* (2006.01)
*A61M 1/36* (2006.01)
*A61M 39/28* (2006.01)

(52) U.S. Cl.
CPC ............ *A61M 1/367* (2013.01); *A61M 39/28* (2013.01); *F16K 7/045* (2013.01); *A61M 2205/18* (2013.01); *A61M 2205/3317* (2013.01)

(58) Field of Classification Search
CPC .. A61M 1/367; A61M 39/28; A61M 2205/18; A61M 2205/3317; F16K 7/045; F16K 7/04
See application file for complete search history.

(56) References Cited

U.S. PATENT DOCUMENTS 2,726,019 A * 12/1955 Moran .................... F16K 7/045
222/445
3,789,876 A * 2/1974 Kempton ............ F16K 37/0033
137/554

(Continued)

FOREIGN PATENT DOCUMENTS

DE 102015213206 A1 1/2017
EP 2517753 A1 10/2012
WO 2016057981 A1 4/2016

OTHER PUBLICATIONS

International Search Report and Written Opinion issued in corresponding International Patent Application No. PCT/EP2018/054182 (with English translation of International Search Report) dated May 9, 2018 (13 pages).

(Continued)

*Primary Examiner* — Craig J Price
*Assistant Examiner* — Andrew J Rost
(74) *Attorney, Agent, or Firm* — Kilyk & Bowersox, P.L.L.C.

(57) ABSTRACT

The invention relates to an apparatus for clamping a hose line, comprising a clamping body 19, an electromagnetic actuation unit 20 for the clamping body and a monitoring device 23 which monitors the position of the clamping body, (Continued)

Figure 1:
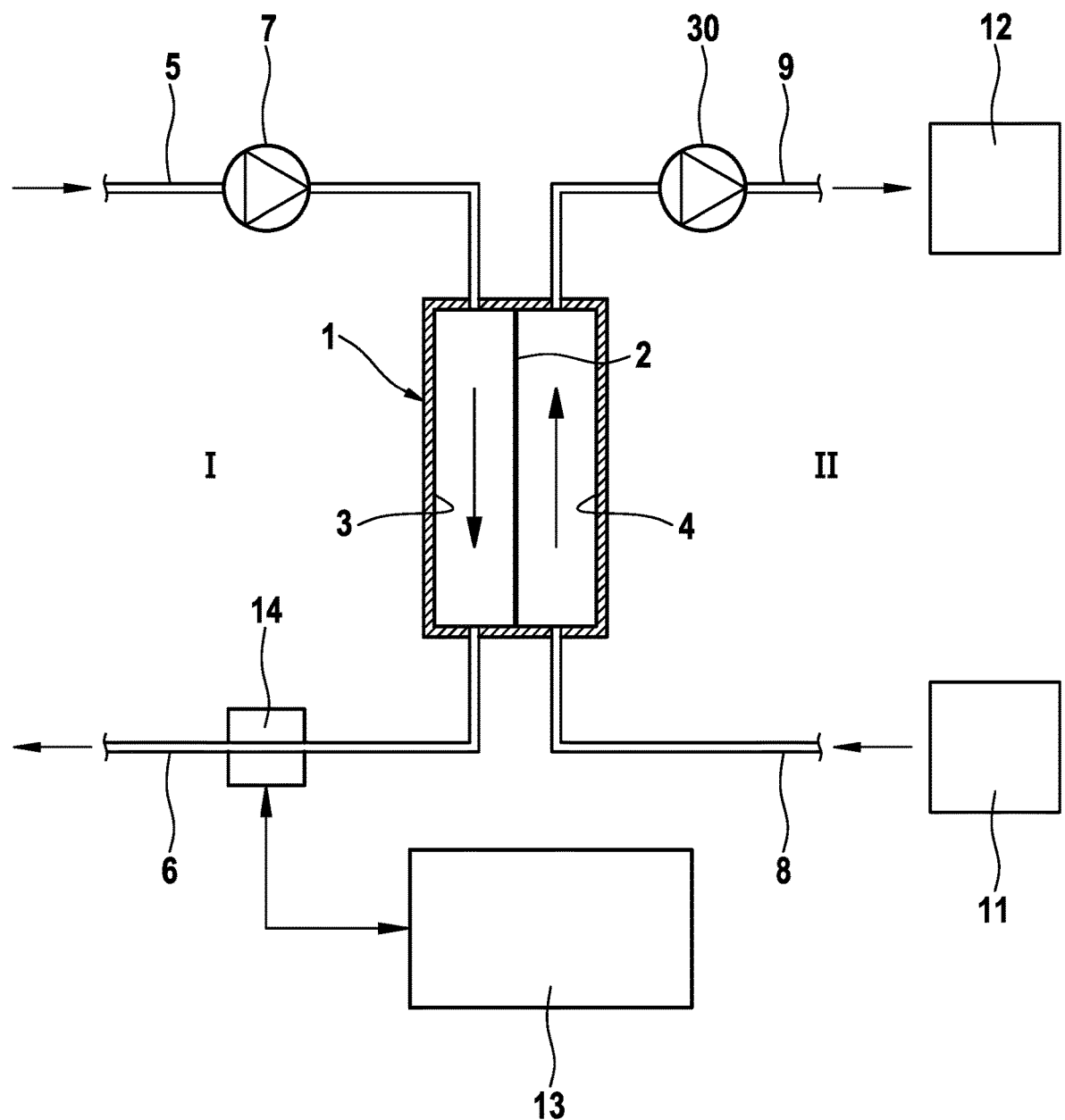

the actuation unit 20 comprising a coil 21 for generating a magnetic field. The invention also relates to a medical treatment apparatus, in particular an apparatus for extracorporeal blood treatment, comprising an apparatus 14 for clamping a hose line, and to a method for monitoring an apparatus for clamping a hose line. The monitoring device 23 has a measurement device 24 for measuring an electrical property of the coil 21 that is dependent on the position of the clamping body 19, and an evaluation device 25 for determining the position of the clamping body 19 on the basis of the electrical property of the coil. Given that only one electrical property of the coil 21 is monitored, an additional mechanical component is not required for monitoring. In a preferred embodiment of the invention, the inductance L of the coil 21 is an electrical property that is dependent on the position of the clamping body 19. A measurement device 25 is provided in order to measure the inductance L of the coil.

17 Claims, 4 Drawing Sheets

(56) References Cited

U.S. PATENT DOCUMENTS

| | | | | |
|---|---|---|---|---|
| 4,496,133 | A * | 1/1985 | Sule | F16K 7/045 |
| | | | | 137/595 |
| 4,993,456 | A * | 2/1991 | Sule | F16K 7/045 |
| | | | | 137/554 |
| 8,622,365 | B2 * | 1/2014 | Fukano | F16K 7/045 |
| | | | | 251/7 |
| 9,782,577 | B2 * | 10/2017 | Bedingfield | A61M 1/28 |
| 2001/0019117 | A1 | 9/2001 | Schoeb | |
| 2007/0246015 | A1 * | 10/2007 | Moreno | F16K 31/06 |
| | | | | 123/458 |
| 2010/0188667 | A1 | 7/2010 | Weatherbee et al. | |

OTHER PUBLICATIONS

International Preliminary Report on Patentability issued in corresponding International Patent Application No. PCT/EP2018/054182 dated Sep. 6, 2019 (8 pages).

* cited by examiner

DEVICE FOR CLAMPING A HOSE LINE, MEDICAL TREATMENT DEVICE WITH A DEVICE FOR CLAMPING A HOSE LINE, AND METHOD FOR MONITORING A DEVICE FOR CLAMPING A HOSE LINE

This application is a National Stage Application of PCT/EP2018/054182, filed Feb. 20, 2018, which claims priority to German Patent Application No. 10 2017 001 744.1, filed Feb. 23, 2017.

The invention relates to an apparatus for clamping a hose line, comprising a clamping body, an electromagnetic actuation unit for the clamping body, and a monitoring device which monitors the position of the clamping body, the actuation unit comprising a coil for generating a magnetic field. The invention also relates to a medical treatment apparatus, in particular an apparatus for extracorporeal blood treatment, comprising an apparatus for clamping a hose line, and to a method for monitoring an apparatus for clamping a hose line.

The extracorporeal blood circuit of known blood treatment apparatuses comprises an arterial hose line, which leads to the blood chamber of the blood treatment element, e.g. a dialyser, and a venous hose line, which leads out of the blood chamber. The hose lines of the extracorporeal blood treatment apparatus are generally provided as a hose set intended for single use (disposable). The blood treatment apparatuses have a blood pump, which is generally arranged upstream of the blood chamber of the blood treatment element, in order to ensure sufficient blood flow in the extracorporeal blood circuit.

In order to interrupt the blood flow, the blood treatment apparatuses have automatic hose clamps, for example a venous hose clamp for interrupting the blood flow in the venous blood line. Known automatic hose clamps comprise an axially movable clamping body which is resiliently biased on an abutment surface. The clamping body is actuated by an electromagnetic actuation unit comprising a coil for generating a magnetic field which exerts a force on the clamping body.

When the blood treatment apparatuses are being set up, the hose line is inserted into the hose clamp between the clamping body and the abutment surface such that the hose line is clamped. So as to carry out the blood treatment, the hose clamp is automatically opened so that fluid can flow through the hose line.

The venous hose clamp for interrupting the blood flow in the venous blood line is crucial to the safe operation of the blood treatment apparatuses. In the event of a fault, the venous hose clamp is automatically closed, such that the blood flow is interrupted. If this does not occur, the patient could bleed to death. This assumes, however, that the hose line was also correctly inserted into the hose clamp when the blood treatment apparatus was being set up. If this were not the case, the hose clamp would not have any effect.

Hose sets used for blood treatment generally comprise a relatively high number of hose lines. Therefore, inserting the hose set into the blood treatment apparatus in the correct manner requires a certain amount of experience. Although an incorrectly inserted hose line can be detected by means of a pressure hold test, which is carried out prior to the blood treatment and is used to check the integrity of the dialyser, this pressure hold test does not always make it possible to reliably detect, under all operating conditions, whether the hose line is inserted into the hose clamp in the correct manner.

The prior art includes apparatuses for clamping hose lines, having a switch that is closed by the hose line when said hose line is inserted into the hose clamp. A drawback of this is that an additional mechanical component is required in order to monitor the hose line. This increases the production costs. The installation of a switch also produces, as a result of the design thereof, projecting parts and housing gaps, meaning that cleaning is made more difficult. Furthermore, integrating a switch in the hose clamp only makes it possible to detect two operating states, i.e. whether or not a hose line is inserted into the hose clamp.

The object of the invention is to provide an apparatus for clamping a hose line, having a monitoring device which can at least reliably detect without the need for additional mechanical components whether or not a hose line is inserted into the hose clamp.

The object of the invention is also to provide an apparatus for clamping a hose line, having a monitoring device which can reliably detect without the need for additional mechanical components whether the apparatus for clamping a hose line is free of electrical defects, for example a break in the coil as a result of thermal stress.

The object of the invention is also to provide an apparatus for clamping a hose line, having a monitoring device which can reliably detect without the need for additional mechanical components whether the apparatus for clamping a hose line is free of mechanical obstructions preventing the valve from opening/closing, for example mechanical jamming or a foreign object that may have been accidentally added by the user.

These objects are achieved according to the invention by the features of the independent claims. The dependent claims relate to advantageous embodiments of the invention.

The invention relates to monitoring an electrical property of the coil that is dependent on the position of the clamping body.

The monitoring device of the apparatus for clamping a hose line according to the invention has a measurement device for measuring an electrical property of the coil that is dependent on the position of the clamping body, and an evaluation device for determining the position of the clamping body on the basis of the electrical property of the coil. Given that only one electrical property of the coil is monitored, an additional mechanical component is not required for monitoring. This results in reduced production costs. Moreover, projecting parts or gaps in an additional mechanical component do not make it more difficult to clean the apparatus.

In an embodiment of the invention, the inductance of the coil is an electrical property that is dependent on the position of the clamping body. The inductance of the coil is determined by the spatial arrangement of the coil and the clamping body. A measurement device is provided in order to measure the inductance of the coil. In order to detect the position of the clamping body, absolute values need not be determined for the inductance of the coil, but it can be sufficient instead to determine relative values therefor. In this respect, evaluation of the measurement result has proven to be simple.

When mention is made to a clamping body or a coil in this context, it is not to be understood that the apparatus for clamping a hose line has just one single clamping body and/or just one single coil. The apparatus may also have a plurality of clamping bodies that act on the hose line from one and/or more sides. A clamping body may be actuated by the magnetic field of one or more coils.

The clamping body can move axially and/or rotationally in order to clamp the hose line. In a preferred embodiment, an axially movable anchor is provided as the clamping body and a hollow coil is provided as the coil, which the clamping body penetrates. The inductance of the coil increases as the penetration depth of the clamping body designed as an anchor increases. Therefore, inductance is an electrical variable that is dependent on the position of the clamping body.

The clamping body is preferably resiliently biased into a position in which it clamps the hose line, such that the hose line is clamped when the coil is not supplied with current. Therefore, the main position of the hose clamp is a position in which it clamps the hose line. This means that the hose clamp cannot be opened unintentionally as a result of the power supply failing.

In a further embodiment, the monitoring device comprises an evaluation device which comprises a comparison device that is designed such that the electrical property of the coil is compared with at least one specified threshold value. The evaluation device is designed such that a conclusion is made regarding the position assumed by the clamping body when the electrical property exceeds or falls below the at least one threshold value. In this embodiment, it is not necessary to determine absolute values for the electrical property of the coil. In order to evaluate the measurement results, it is sufficient for the measured values to be compared with one or more threshold values that are characteristic of a particular position of the clamping body. For example, it can be checked whether the measured values are within or outside a threshold value range that is characteristic of the relevant position of the clamping body. These threshold values can be calculated empirically and stored in a memory of the evaluation device.

The apparatus for clamping a hose line according to the invention makes it possible to detect a plurality of operating states in which the clamping body assumes a particular position.

The comparison device can be designed such that, if the electrical property of the coil is below a first upper threshold value and/or above a first lower threshold value, it is concluded that a first position has been assumed in which the valve body assumes a completely open position in which a hose line can be inserted into the apparatus for clamping the hose line.

Furthermore, the comparison device can be designed such that, if the electrical property of the coil is below a second upper threshold value and/or above a second lower threshold value, it is concluded that a second position has been assumed in which the valve body assumes a position in which a hose line inserted into the apparatus for clamping the valve body is clamped.

Moreover, the comparison device can be designed such that, if the electrical property of the coil is below a third upper threshold value and/or above a third lower threshold value, it is concluded that a third position has been assumed in which the valve body assumes a completely closed position in which a hose line is not inserted into the apparatus for clamping the hose line.

The first upper and lower threshold values, the second upper and lower threshold values and the third upper and lower threshold values define, in each case, a threshold value range which includes the measured value for inductance in one of the three operating states. Therefore, if the variable that is dependent on the position of the clamping body is the inductance of the coil, the first upper threshold value and the first lower threshold value may be greater than the second upper threshold value and the second lower threshold value, and the second upper threshold value and the second lower threshold value may be greater than the third upper threshold value and the third lower threshold value.

To simplify measurement of the inductance, in a further particularly preferred embodiment, the measurement device comprises a voltage source for generating a test voltage which is applied to the coil such that a current flows through the coil, and a voltmeter which measures the change over time in the voltage which drops across the coil. In this embodiment, the evaluation device is designed such that absolute values are not calculated for the inductance, but the profile over time of the voltage drop across the coil is instead evaluated as a variable that correlates with the inductance of the coil.

The comparison device of the evaluation device is preferably designed such that the decrease in voltage in a specified time period is compared with at least one threshold value.

Instead of measuring the voltage drop across the coil, it is also possible to evaluate the change in the current flowing through the coil. It is also possible to evaluate other electrical variables instead of the inductance of the coil. For example, it is also possible to form an electrical resonant circuit by connecting a capacitor in parallel with the coil, the resonant frequency of which circuit is determined from the inductance of the coil, which is dependent on the position of the clamping body.

Instead of taking the measurement using a test voltage, the measurement can also be taken by switching the valve (open/close) by means of the switching voltage.

In a further embodiment, the impedance of the system can also be determined as the electrical property of the coil. For this purpose, an AC voltage is applied as the test voltage and the average value over time for the system resistance is determined.

The monitoring device preferably comprises a display device which is designed such that the position assumed by the clamping body is displayed. The display device may be a screen for example.

An alarm device can also be provided which is designed such that an alarm is emitted if the clamping body assumes a particular position, for example a position in which the hose line is not inserted into the apparatus.

The monitoring device can also generate a control signal if a particular operating state is detected, for example if the hose line is not inserted into the clamping apparatus, such that intervention in the machine control of the blood treatment apparatus can be made, for example the blood pump can be stopped.

The apparatus for extracorporeal blood treatment according to the invention may comprise one or more of the apparatuses for clamping a hose line, in particular the venous hose line of the extracorporeal blood circuit. The monitoring device of the apparatus for clamping a hose line may be a component of the central control and arithmetic unit of the blood treatment apparatus.

Figure 2:
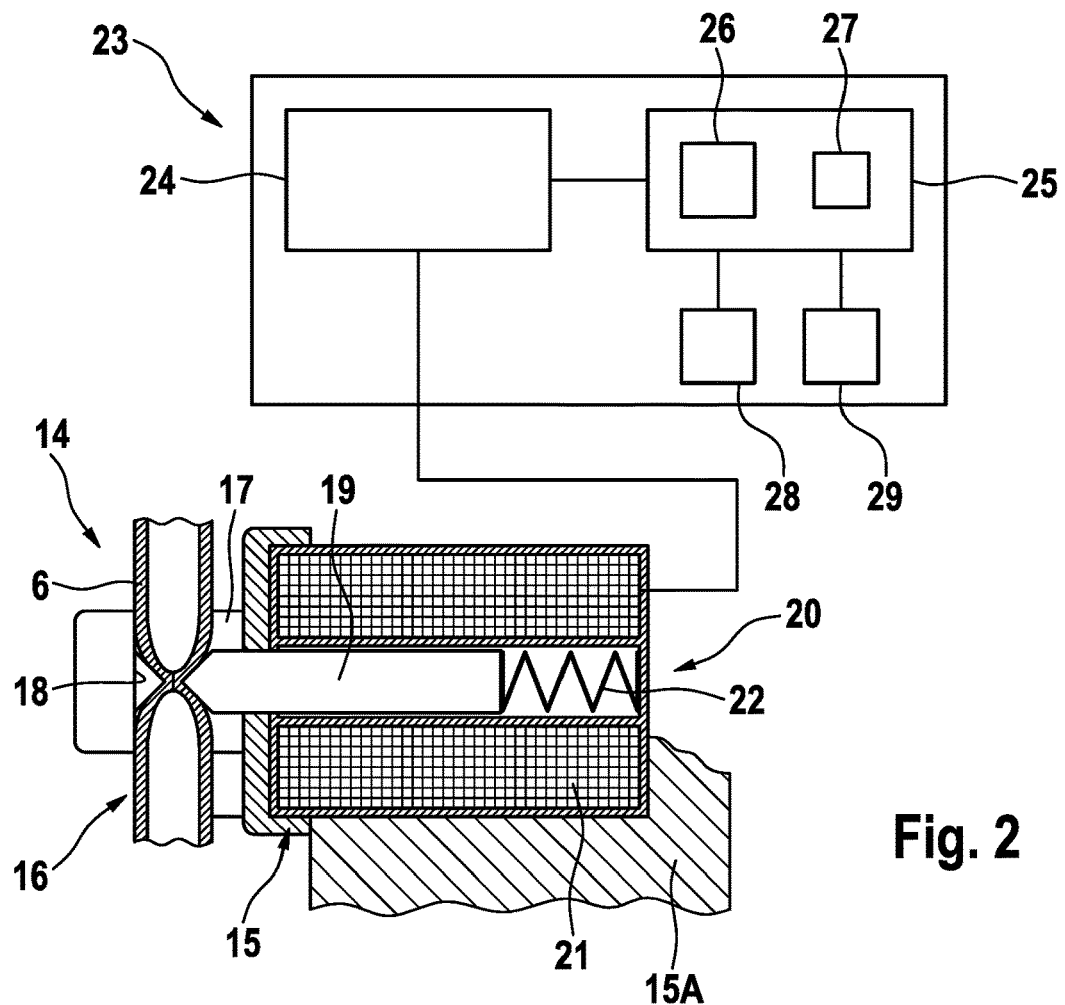
Figure 3:
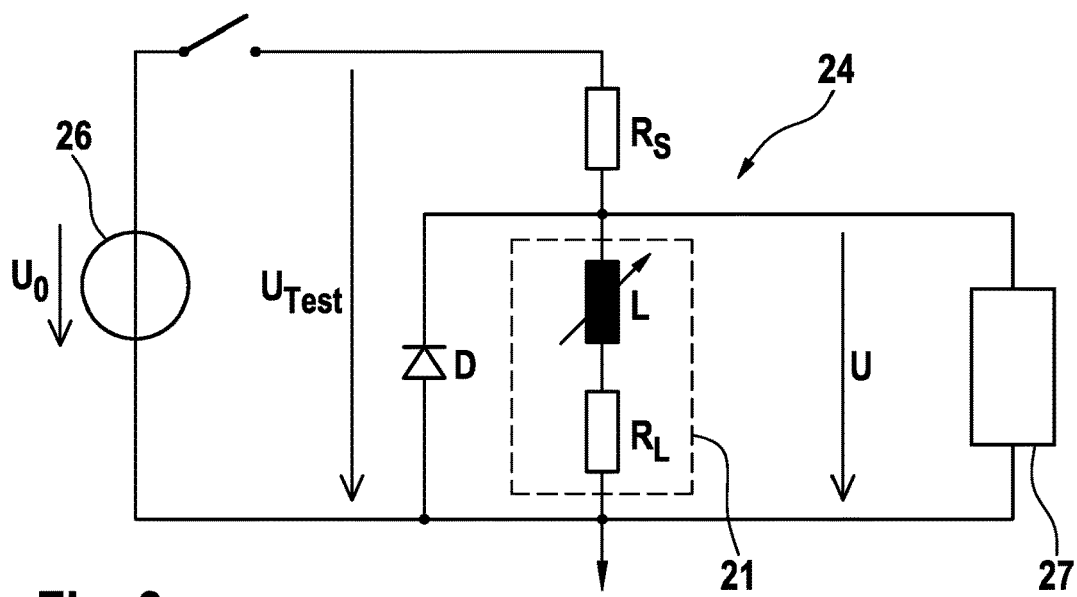
Figure 4A:
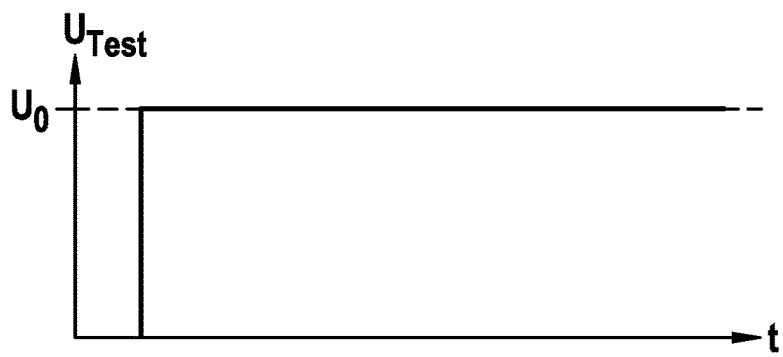
Figure 4B:
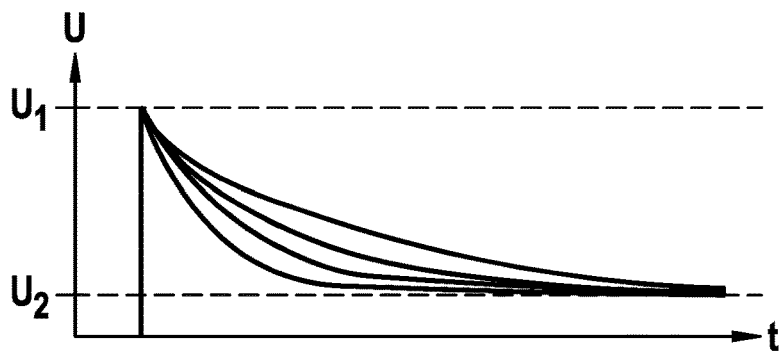
Figure 5A:
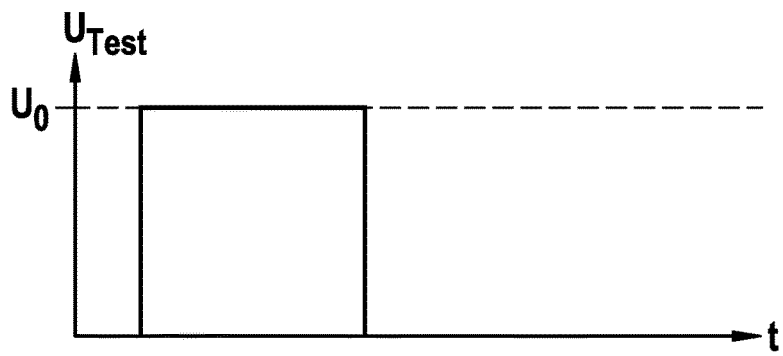
Figure 5B:
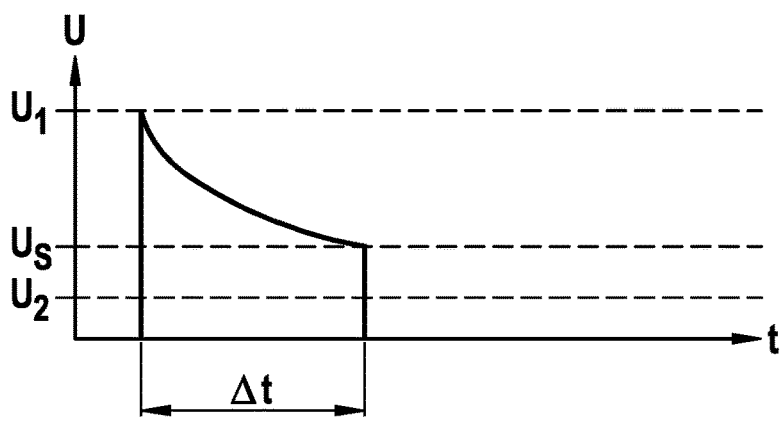
Figure 6:
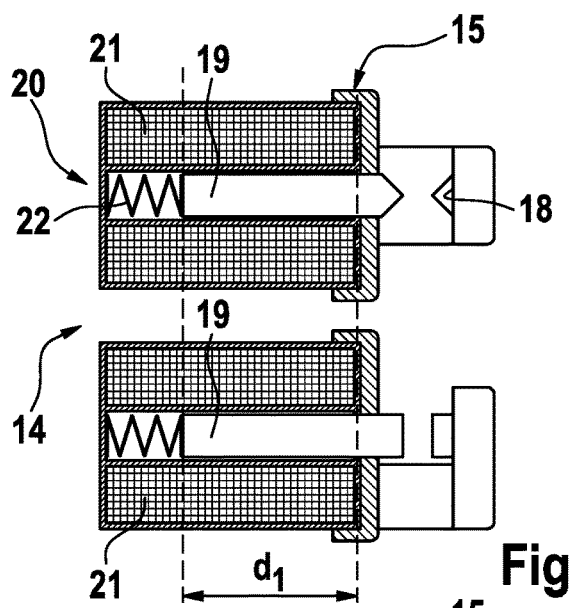
Figure 6:
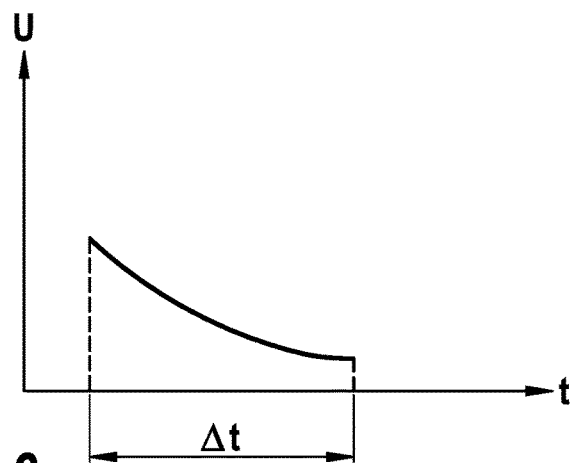
Figure 7:
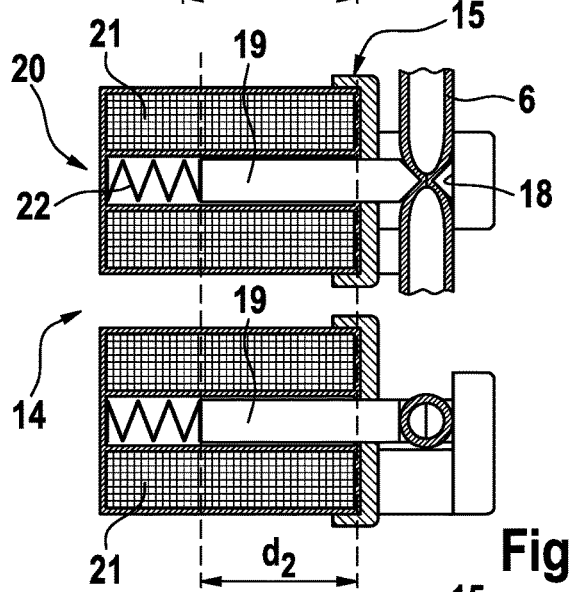
Figure 7:
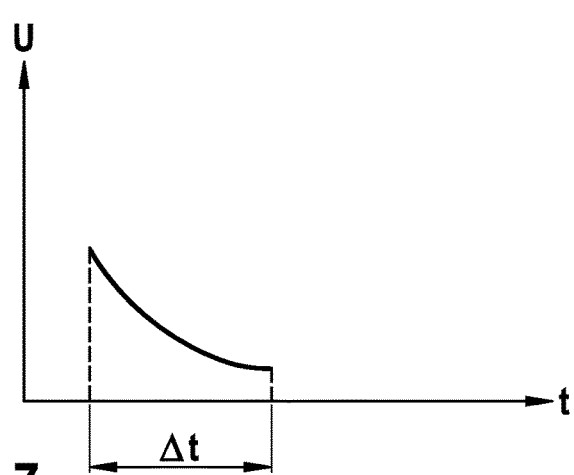
Figure 8:
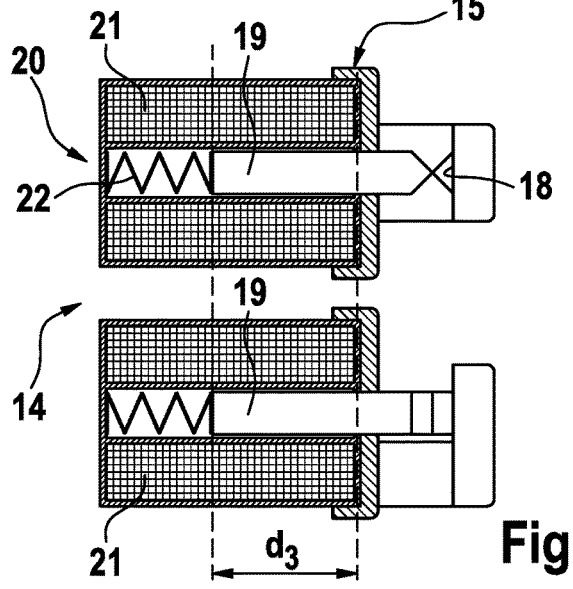
Figure 8:
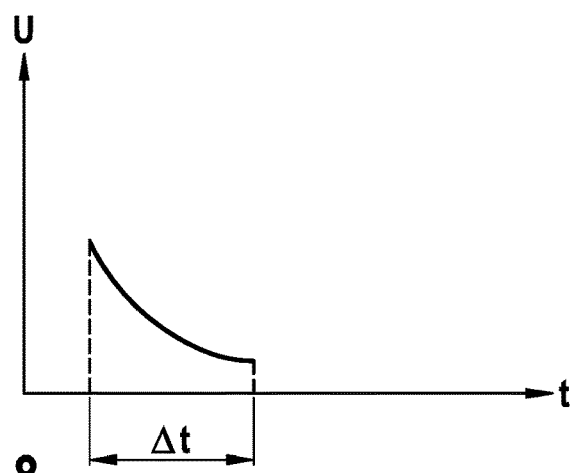

An embodiment of the invention is described in more detail below with reference to the drawings,
in which:

FIG. 1 is a simplified schematic view of an apparatus for extracorporeal blood treatment according to the invention that has an apparatus for clamping a hose line according to the invention, FIG. 2 is a simplified schematic view of the apparatus for clamping a hose line according to the invention, FIG. 3 shows a circuit for determining the inductance of the coil of the actuation unit for the clamping body of the apparatus for clamping a hose line, FIGS. 4A and 4B show the profile over time of the test voltage and the voltage drop across the coil for various inductance values, FIGS. 5A and 5B show the profile over time of the test voltage and the voltage drop across the coil in a time period during which the test voltage has dropped to a specified threshold value, FIG. 6 shows the apparatus for clamping a hose line in a first operating state and the associated profile over time of the voltage drop measured across the coil, FIG. 7 shows the apparatus for clamping a hose line in a second operating state and the associated profile over time of the voltage drop, and FIG. 8 shows the apparatus for clamping a hose line in a third operating state and the associated profile over time of the voltage drop measured across the coil.

In the present embodiment, the medical treatment apparatus is an extracorporeal blood treatment apparatus, in particular a haemodialysis apparatus, which has an extracorporeal blood circuit I comprising a dialyser 1 which is divided into a blood chamber 3 and a dialysate chamber 4 by a semi-permeable membrane 2. An arterial blood line 5, in which a blood pump 7 is arranged, leads from a patient to an inlet of the blood chamber 3, whilst a venous blood line 6 leads from an outlet of the blood chamber to the patient. The arterial and venous blood lines 5, 6 are flexible hose lines of a hose set intended for single use (disposable).

The fresh dialysate is provided in a dialysate source 10. A dialysate supply line 8 leads from the dialysate source 10 to an inlet of the dialysate chamber 4 of the dialyser 1, whilst a dialysate discharge line 9 leads from an outlet of the dialysate chamber 4 to a drain 12. A dialysate pump 30 is arranged in the dialysate discharge line 9.

The individual components of the blood treatment apparatus are controlled by means of a central control and arithmetic unit 13.

An apparatus 14 (shown only schematically in FIG. 1) for clamping the venous hose line 6 is provided in order to interrupt the blood flow to the patient. When the blood treatment apparatus is being set up, the venous hose line 6 is inserted into the apparatus 14 for clamping the hose line. The apparatus 14 for clamping the hose line is described in more detail below.

FIG. 2 is a simplified schematic view of the apparatus 14 for clamping the hose line. The apparatus comprises a housing body 15 which may be a component of the housing 15A of the blood treatment apparatus. The housing body 15 comprises a receiving portion 16 for the hose line 6, comprising a bearing surface 17 on which the hose line inserted into the apparatus rests. The hose line 6 is between an abutment surface 18 of the housing body 15 and a clamping body 19 which is guided in the housing body 15 so as to be axially movable. The clamping body 19 is actuated by an electromagnetic actuation unit 20 which is designed as a linear magnet (solenoid) which comprises a cylindrical hollow coil 21. The clamping body 19 is designed as an anchor which penetrates the cylindrical hollow coil 21 of the linear magnet and is resiliently biased towards the abutment surface 18 by a compression spring 22. When a current flows through the hollow coil 21, a magnetic field is generated which pulls the clamping body 19 back into the hollow coil 21 counter to the spring force. The electromagnetic actuation unit 20 is controlled by the central control and arithmetic unit 13.

Moreover, the apparatus 14 for clamping the hose line has a monitoring device 23 which comprises a measurement device 24 and an evaluation device 25. Measurement device 24 and evaluation device 25 are only shown schematically in FIG. 2. In the present embodiment, the measurement device 24 is designed as a measurement device for measuring the inductance of the coil.

FIG. 3 shows a circuit illustrating the function of the measurement device 24. The coil 21 is represented in the circuit by an equivalent circuit diagram. The coil 21 has an ohmic resistor $R_L$ and an inductance L that is dependent on the penetration depth d of the clamping body 19 in the coil.

The monitoring device 23, in particular the evaluation device 25 thereof, can have, for example, a general processor, a digital signal processor (DSP) for continuously processing digital signals, a microprocessor, an application-specific integrated circuit (ASIC), an integrated circuit consisting of logic elements (FPGA) or other integrated circuits (IC) or hardware components, in order to perform the individual method steps for controlling the monitoring device. A data processing program (software) can run on the hardware components in order to carry out the method steps.

The monitoring device 23 may form an independent assembly, the measurement device 24 and evaluation device 25 being independent of the rest of the components of the blood treatment apparatus. The monitoring device 23 or parts of the monitoring device can however also be component parts of the components of the blood treatment apparatus. For example, the evaluation device 25 may be a component of the central control and arithmetic unit 13 of the blood treatment apparatus.

The measurement device 24 comprises a voltage source 26 for generating a test voltage $U_{Test}=U_0$ and a voltmeter 27 for measuring the voltage U across the coil. The test voltage $U_{Test}$ is applied to a series circuit consisting of a series resistor $R_S$ and the coil 21. As a result, a current flows through the coil 21, and therefore a magnetic field is generated. The level of the test voltage $U_{Test}$ is such that the clamping body 19 is not moved during the test. The voltage U is measured across the coil 21 using the voltmeter 27, which voltage is evaluated by the evaluation device 25.

FIGS. 4A and 4B show the test voltage $U_{Test}=U_0$ as a function of time t and the voltage U across the coil 21, respectively. The voltage drops from a value $U_1$ to a value $U_2$. An exponential decrease in the voltage U is shown, the time constant being dependent on the inductance L of the coil. The higher the inductance L, the lower the amount by which the voltage U drops from the value $U_1$ in a specified time period. FIGS. 5A and 5B show the profile over time of the voltage U for the test voltage $U_{Test}=U_0$. The time period $\Delta t$ during which the voltage has dropped to the threshold value $U_S$ is dependent on the inductance L of the coil 21. The longer the time period $\Delta t$, the higher the inductance L.

The evaluation device 25 comprises a comparison device 26 which compares the measured voltage U with a plurality of threshold values which, in the present embodiment, define three threshold value ranges. The threshold values are read out from a memory 27 of the evaluation device 25.

The comparison device 26 is configured such that it can be concluded that a first operating state has been adopted, in which the clamping body 19 assumes a completely open position (FIG. 6). In this position, the hose line 6 can be inserted into the apparatus 14 for clamping said hose line. This requires the clamping body 19 to be manually pushed back into the spring 22 counter to the spring force. In this position, the penetration depth is $d=d_1$. At penetration depth $d_1$, the inductance is $L=L_1$. There is a time period, $\Delta t_1$, during which the voltage has dropped to the threshold value $U_S$, and this is a measure for the inductance L. The evaluation device 25 checks whether $\Delta t_1$ is within a first threshold value range defined by a first upper threshold value and a first lower threshold value. If $\Delta t_1$ is within the first threshold value range, it is concluded that the first operating state has been adopted.

The comparison device 26 is also configured such that it can be concluded that a second operating state has been adopted, in which the clamping body 19 assumes a position in which a hose line 6 inserted into the apparatus 14 for clamping a hose line is clamped (FIG. 7). In this position, the penetration depth is $d=d_2$ ($d_2<d_1$). At penetration depth $d_2$, the inductance is $L=L_2$. There is a time period, $\Delta t_2$, during which the voltage has dropped to the threshold value $U_S$, and this is a measure for the inductance L. The evaluation device 25 checks whether $\Delta t_2$ is within a second threshold value range defined by a second upper threshold value and a second lower threshold value. If $\Delta t_2$ is within the second threshold value range, it is concluded that the second operating state has been adopted.

The comparison device 26 is also configured such that it can be concluded that a third operating state has been adopted in which the clamping body 19 assumes a completely closed position in which a hose line 6 is not inserted into the apparatus 14 for clamping a hose line (FIG. 8). In this position, the penetration depth is $d=d_3$ ($d_3<d_2$). At penetration depth $d_3$, the inductance is $L=L_3$. There is a time period, $\Delta t_3$, during which the voltage has dropped to the threshold value $U_S$, and this is a measure for the inductance L. The evaluation device 25 checks whether $\Delta t_3$ is within a third threshold value range defined by a third upper threshold value and a third lower threshold value. If $\Delta t_2$ is within the third threshold value range, it is concluded that the third operating state has been adopted.

In the present embodiment, threshold value ranges are defined, it being checked whether the time period $\Delta t$ is within or outside the threshold value range. In order to detect the different operating states, it is however also possible to compare the time period $\Delta t$ with just one upper threshold value and one lower threshold value. If the time period $\Delta t$ is above the upper threshold value, it is concluded that the first operating state (FIG. 6) has been adopted, whereas it is concluded that the third operating state (FIG. 8) has been adopted if the time period $\Delta t$ is below the lower threshold value. If the time period $\Delta t$ is between the upper and lower threshold values, it is concluded that the second operating state (FIG. 7) has been adopted.

On the basis of the detected operating state, the evaluation device 25 generates a signal assigned to the relevant operating state. The signals from the evaluation device 25 are received by a display device 28, by means of which the relevant operating state is displayed, for example on a screen by means of a corresponding symbol. Furthermore, the signals can be received by an alarm device 29 which emits an acoustic and/or visual and/or tactile alarm when a particular operating state has been adopted. For example, an alarm may be emitted if the hose line 6 is not inserted into the apparatus at the start of the blood treatment, i.e. if the first or third operating state is detected. The signals can also be received by the central control and arithmetic unit 13 of the blood treatment apparatus, which unit generates control signals according to the operating state. For example, the control and arithmetic unit 13 can be configured such that a control signal is generated for intervention in the machine control if the control and arithmetic unit receives the signal for the second operating state (FIG. 7). For example, the control and arithmetic unit 13 can only enable the blood treatment once the signal for the second operating state (FIG. 7) has been received, i.e. it cannot enable the blood treatment if the signal for the first or third operating state (FIGS. 6 and 8) is received.

The invention claimed is:

1. A method for monitoring an apparatus for clamping a hose line, the apparatus comprising a clamping body configured to move into a position in which the clamping body clamps the hose line and into a position in which the clamping body releases the hose line, and an electromagnetic actuation unit for the clamping body, the electromagnetic actuation unit comprising a coil for generating a magnetic field that exerts a force on the clamping body such that the clamping body moves, wherein
   an electrical property of the coil, which is dependent on the position of the clamping body, is measured, and a conclusion is made regarding the position of the clamping body on the basis of the electrical property of the coil,
   the electrical property of the coil is compared with at least one specified threshold value by using an evaluation device that comprises a comparison device, the conclusion being made regarding the position assumed by the clamping body when the electrical property exceeds or falls below the at least one specified threshold value, and
   if the comparison made by the comparison device determines that the electrical property of the coil is below an upper threshold value and/or above a lower threshold value, the evaluation device concludes that a completely closed position has been assumed in which the clamping body assumes a completely closed position in which the hose line is not in the apparatus.

2. The method according to claim 1, wherein the electrical property of the coil, which is dependent on the position of the clamping body, is an inductance L of the coil.

3. The method according to claim 1, wherein,
   if the electrical property of the coil is below a second upper threshold value and/or above a second lower threshold value, it is concluded that a first position has been assumed in which the clamping body assumes a completely open position and is capable of receiving the hose line, and/or
   if the electrical property of the coil is below a third upper threshold value and/or above a third lower threshold value, it is concluded that a second position has been assumed in which the clamping body assumes a position in which the hose line is in the apparatus.

4. A method for monitoring an apparatus for clamping a hose line, the apparatus comprising a clamping body configured to move into a position in which the clamping body clamps the hose line and into a position in which the clamping body releases the hose line, and an electromagnetic actuation unit for the clamping body, the actuation unit comprising a coil for generating a magnetic field that exerts a force on the clamping body such that the clamping body moves, wherein
   an electrical property of the coil, which is dependent on the position of the clamping body, is measured, and a conclusion is made regarding the position of the clamping body on the basis of the electrical property of the coil, and
   a test voltage is applied to the coil such that a current flows through the coil and a change over time in the voltage that drops across the coil is measured, and a profile over time of the voltage drop across the coil is evaluated.

5. An apparatus for clamping a hose line that is in the apparatus, comprising:
   a clamping body configured to move into a position in which the clamping body clamps the hose line, and into a position in which the clamping body releases the hose line;
   an electromagnetic actuation unit for the clamping body, comprising a coil for generating a magnetic field that exerts a force on the clamping body such that said clamping body is movable; and
   a monitoring device that monitors the position of the clamping body, wherein
   the monitoring device comprises a measurement device for measuring an electrical property of the coil, which is dependent on the position of the clamping body, and an evaluation device for determining the position of the clamping body on the basis of the electrical property of the coil,
   the evaluation device comprises a comparison device designed such that the electrical property of the coil is compared with at least one specified threshold value, the evaluation device being designed such that, when the electrical property exceeds or falls below the at least one specified threshold value, a conclusion is made regarding the position assumed by the clamping body, and
   the comparison device is designed such that, if the electrical property of the coil is below an upper threshold value and/or above a lower threshold value, it is concluded that a completely closed position has been assumed in which the clamping body assumes a completely closed position in which the hose line is not in the apparatus.

6. The apparatus according to claim 5, wherein the clamping body is an axially movable anchor, and the coil is a hollow coil that the clamping body penetrates.

7. The apparatus according to claim 5, wherein the clamping body is resiliently biased into the position in which the clamping body clamps the hose line.

8. The apparatus according to claim 5, wherein the electrical property of the coil, which is dependent on the position of the clamping body, is an inductance L of the coil, and the measurement device is a measurement device for measuring the inductance L of the coil.

9. The apparatus according to claim 5, wherein the comparison device is designed such that, if the electrical property of the coil is below a second upper threshold value and/or above a second lower threshold value, it is concluded that a first position has been assumed in which the clamping body assumes a completely open position and is capable of receiving the hose line.

10. The apparatus according to claim 5, wherein the comparison device is designed such that, if the electrical property of the coil is below a third upper threshold value and/or above a third lower threshold value, it is concluded that a second position has been assumed in which the clamping body assumes the position in which the hose line is in the apparatus and the hose line is clamped.

11. The apparatus according to claim 5, wherein the monitoring device comprises a display device designed such that the position assumed by the clamping body is displayed.

12. The apparatus according to claim 5, wherein the monitoring device comprises an alarm device designed such that an alarm is emitted if the clamping body assumes a particular position.

13. A medical treatment apparatus comprising the apparatus according to claim 5, for clamping the hose line.

14. A medical treatment apparatus for extracorporeal blood treatment, comprising the apparatus according to claim 5 for clamping the hose line, wherein the hose line is a venous hose line of an extracorporeal blood circuit of the medical treatment apparatus.

15. The apparatus according to claim 5, wherein the evaluation device further comprises a memory and the at least one specified threshold value is stored in the memory.

16. An apparatus for clamping a hose line that is in the apparatus, comprising:
   a clamping body configured to move into a position in which the clamping body clamps the hose line, and into a position in which the clamping body releases the hose line;
   an electromagnetic actuation unit for the clamping body, comprising a coil for generating a magnetic field that exerts a force on the clamping body such that said clamping body is movable; and
   a monitoring device that monitors the position of the clamping body, wherein
   the monitoring device comprises a measurement device for measuring an electrical property of the coil, which is dependent on the position of the clamping body, and an evaluation device for determining the position of the clamping body on the basis of the electrical property of the coil,
   the evaluation device comprises a comparison device designed such that the electrical property of the coil is compared with at least one specified threshold value, the evaluation device being designed such that, when the electrical property exceeds or falls below the at least one specified threshold value, a conclusion is made regarding the position assumed by the clamping body, and
   the measurement device comprises a voltage source for generating a test voltage applied to the coil such that a current flows through the coil, and a voltmeter that measures a change over time in the voltage that drops across the coil, the evaluation device being designed such that a profile over time of the voltage drop across the coil is evaluated.

17. The apparatus according to claim 16, wherein the comparison device is designed such that a decrease in voltage in a specified time period $\Delta t$ is compared with the at least one specified threshold value.

* * * * *